United States Patent
Crooks et al.

(10) Patent No.: US 6,703,406 B2
(45) Date of Patent: Mar. 9, 2004

(54) 2,6-DISUBSTITUTED PIPERIDINES AS MODULATORS OF NICOTINIC ACETYLCHOLINE RECEPTOR MEDIATED NEUROTRANSMITTER RELEASE, UPTAKE AND STORAGE

(75) Inventors: Peter A. Crooks, Lexington, KY (US); Linda Dwoskin, Lexington, KY (US); Dennis Keith Miller, Lexington, KY (US); Vladimir P. Grinevich, Lexington, KY (US); Seth Davin Norrholm, Lexington, KY (US); Guangrong Zheng, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 10/163,633

(22) Filed: Jun. 7, 2002

(65) Prior Publication Data

US 2004/0019081 A1 Jan. 29, 2004

Related U.S. Application Data

(63) Continuation-in-part of application No. 09/628,557, filed on Jul. 28, 2001, now Pat. No. 6,455,543.
(60) Provisional application No. 60/146,144, filed on Jul. 30, 1999.

(51) Int. Cl.[7] .................... A61K 31/445; C07D 211/18; C07D 211/20

(52) U.S. Cl. .................... 514/317; 514/331; 546/192; 546/229

(58) Field of Search .................. 514/317, 331; 546/192, 229

(56) References Cited

U.S. PATENT DOCUMENTS 6,455,543 B1 * 9/2002 Dwoskin et al. ............ 514/317

OTHER PUBLICATIONS

P. Crooks et al. "Inhibition of Nicotine Evoked [$^3$H]Dopamine Release by Pyridino N–Substituted Nicotine Analogues: A New Class of Nicotinic Antagonist" Drug Development Research. 1995. 36:91–102.

L. Teng et al. "Lobeline Displaces [$^3$H] Dihydrotetrabenazine Binding and Release [$^3$H] Dopamine from Rat Striatal Synaptic Vesicles: Comparison with d–Amphetamine" Journal of Neurochemistry. vol. 71. No. 1. Jul. 1998. 258–265.

L. Teng et al. "Lobeline and Nicotine Evoke [$^3$H] Overflow from Rat Striatal Slices Preloaded with [$^3$H] Dopamine: Differential Inhibition of Synaptosomal and Vesicular [$^3$H] Domapine Uptake" The Journal of Pharmacology and Experimental Therapeutics. Williams & Wilkins. vol. 280. No. 3. 1997. 1432–1444.

Y. Cheng et al. "Relationship between the inhibition constant ($K_1$) and the concentration of inhibitor which casuses 50 per cent inhibition ($I_{50}$) of an enzymatic reaction" Biochemical Pharmacology. vol. 22. No. 23. Dec. 1, 1973. 3099–3108.

Michael Decker et al. "Effects of Lobeline, a Nicotinic Receptor Agonist, on Learning and Memory" Pharmacology Biochemistry and Behavior. vol. 45. 1993. 571–576.

Carmelo Romano et al. "Stereospecific Nicotine Receptors on Rat Brain Membranes" Science. vol. 210. Nov. 7, 1980. 647–650.

S. Hamann et al. "Hyperalgesic and Analgesic Actions of Morphine, U50–488, Naltrexone, and (–)–Lobeline in the Rat Brainstem" Pharmacology Biochemistry and Behavior. vol. 47. 1993. 197–201.

Dennis K. Miller et al. "Lobeline inhibits nicotine–evoked [$^3$H]dopamine overflow from rat striatal slices and nicotine–evoked $^{86}$Rb$^+$ efflux from thalamic synaptosomes" Neuropharmacology. 2000. 39:2654–2662.

Patrick M. Lippiello et al. "The Binding of L–[$^3$H] Nicotine to a Single Class of High Affinity Sites in Rat Brain Membranes" Molecular Pharmacology. 29:448–454.

L. Dwoskin et al. "Robust Modulation of [$^3$H] Dopamine Release from Rat Striatal Slices by D–2 Dopamine Receptors" The Journal of Pharmacology and Experimental Therapeutics. 1996. vol. 239. No. 2. 442–453.

M. Marks et al. "Nicotonic Binding Sites in Rat and Mouse Brain: Comparison of Acetylcholine, Nicotine, and α–Bungarotoxin" Molecular Pharmacology. 30:427–436.

E. Broussolle et al. "In Vivo Specific Binding of [$^3$H] 1–Nicotine in the Mouse Brain" Life Sciences. 1989. vol. 44. 1123–1132.

(List continued on next page.)

*Primary Examiner*—Rita Desai
(74) *Attorney, Agent, or Firm*—McDermott, Will & Emery

(57) ABSTRACT

Compounds used for treating dependence on or withdrawal from a drug of abuse, for an eating disorder or for a CNS disease or pathology having the following formulas:

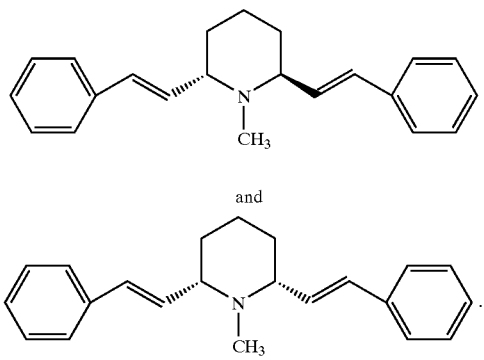

9 Claims, No Drawings

OTHER PUBLICATIONS

L. Dwoskin et al. "(S)–(–)–Cotinine, the Major Brain Metabolite of Nicotine, Stimulates Nicotonic Receptors to Evoke [³H] Dopamine from Rat Striatal Slices in Calcium-Dependent Manner" The Journal of Pharmacology and Experimental Therapeutics. 1999. vol. 288. No. 2. 905–911.

R.B. Barlow et al. "Relations between structure and nicotine–like activity: X–ray crystal structure analysis of (–)–cytisine and (–)–lobeline hydrochloride and a comparison with (–)–nicotine and other nicotine–like compounds" Br. Journal of Pharmacology. 1989. vol. 98. 799–808.

P.B.S. Clark & M. Reuben. "Release of [³H]–noradrenaline from rat hippocampal synaptosomes by nicotine: mediation by different nicotinic receptor subtypes from striatal [³H]–dopamine release" British Journal of Pharmacology. 1996. 117. 595–606.

M. Bradford, "A Rapid and Sensitive Method for the Quantitation of Micogram Quantities of Protein Utilizing the Principle of Protein–Dye Binding" Analytical Biochemistry. 1976. 72. 248–254.

* cited by examiner

2,6-DISUBSTITUTED PIPERIDINES AS MODULATORS OF NICOTINIC ACETYLCHOLINE RECEPTOR MEDIATED NEUROTRANSMITTER RELEASE, UPTAKE AND STORAGE

RELATED APPLICATIONS

This application is a continuation-in-part of application Ser. No. 09/628,557 filed Jul. 28, 2000 now U.S. Pat. No. 6,455,543 which claims priority under 35 U.S.C. § 119(e)(1) to provisional Application No. 60/146,144 filed Jul. 30, 1999.

FIELD OF INVENTION

The present invention relates to the use of the 2,6-disubstituted piperidines, cis-2,6-di-trans-styrylpiperidine and trans-2,6-di-trans-styrylpiperidine, as modulators of nicotinic acetyl-choline receptor mediated neurotransmitter release, uptake and storage. The 2,6-disubstituted piperidines of the present invention can be used for the treatment of drug abuse and withdrawal therefrom, as well as for the treatment of eating disorders such as obesity, and other neuropathologies.

BACKGROUND OF THE INVENTION

Currently, drug discovery is focusing on neuronal nicotinic receptors (nAChRs) as novel targets for the development of therapeutic agents for a wide variety of central nervous system (CNS) diseases including, drug addiction, neuroendocrine, neuropsychiatric and neurological diseases, memory and learning disabilities, eating disorders, and the control of pain, as well as cardiovascular and gastrointestinal disorders. Nicotinic receptor antagonists have good potential as therapeutic agents, since they offer another means of modulating nicotinic receptor function. Nicotinic agonists rapidly desensitize these receptors, essentially inhibiting their function. Thus, inhibition of nicotinic receptor function may be the action, which confers clinical utility, indicating that nicotinic receptor antagonists could also be beneficial in the treatment of diseases for which nicotinic agonists are currently being developed. For example, schizophrenia and drug abuse have both been associated with hyperactivity of CNS dopaminergic systems, and inhibition of nicotinic receptors may be advantageous in reducing such hyperactivity. Furthermore, the availability of subtype-selective nicotinic receptor antagonists will be invaluable agents in both basic and clinical research, with regard to both the treatment and diagnosis of disease. Finally, subtype-selective antagonists will define the role of specific nicotinic receptor subtypes in both physiological function and disease states.

The action of many neuropharmacologically therapeutic agents involve the modulation of dopamine (DA), norepinephrine (NE) and serotonin (5-HT) release, uptake and storage within its respective terminals in the central nervous system (CNS). Most neurotransmitters are stored in synaptic vesicles, which are prominent features of nerve terminals. Concentration into vesicles appears to be responsible for maintaining a ready supply of neurotransmitter available for neuronal exocytotic release into the synaptic cleft. Vesicles also serve the role of protecting the neurotransmitter from metabolic breakdown. One transport site on the vesicle membrane is the vesicular monoamine transporter-2 (VMAT2), whose role is to transport transmitter from the cytosol into the synaptic vesicle. Methoxytetrabenazine (MTBZ) has been used as a radiolabel to probe the interaction of drugs with VMAT2. Once the neurotransmitter is released from the terminal into the synaptic space, it interacts with postsynaptic receptors and subsequently is taken back up into the terminal via the plasma membrane transporter (e.g., the dopamine transporter, DAT and/or the serotonin transporter, SERT). Thus, transporter proteins modify the concentration of neurotransmitter in the cytosolic and vesicular storage pools, thereby having the ability to alter subsequent neurotransmission.

SUMMARY OF THE INVENTION

The present invention is directed to a method of treating an individual who suffers from drug dependence or withdrawal from drug dependence or who suffers from a disease or pathology of the CNS. The method comprises of administering to the individual an effective amount of either cis-2,6-di-trans-styrylpiperidine or trans-2,6-di-trans-styrylpiperidine or an analog thereof, including pharmaceutically acceptable salts of such compounds thereof. As used wherein, the term "effective amount" means an amount of a drug effective to reduce an individual's desire for a drug of abuse or for food, or for alleviating at least one of the symptoms of the disease or pathological symptom of CNS pathology.

The compound can be administered alone, combined with an excipient, or co-administered with a second drug having a similar or synergistic effect. The compound is administered subcutaneously, intramuscularly, intravenously, transdermally, orally, intranasally, intrapulmonary or rectally. The use of cis-2,6-di-trans-styrylpiperidine or trans-2,6-di-trans-styrylpiperidine and derivatives thereof in treating diseases or pathologies of the CNS is implicated. In particular, the treatment of dependencies on such drugs as cocaine, amphetamine, caffeine, nicotine, phencyclidine, opiates, barbiturates, benzodiazepines, cannabinoids, hallucinogens, and alcohol is implicated. Also, the treatment of eating disorders such as obesity is implicated.

In a preferred aspect of the invention, the method of treatment reduces an individual's desire for the drug of abuse or for food by at least one day, but it is also preferred that the treatment method further comprises administering behavior modification counseling to the individual. Although the compound of the present invention is contemplated primarily for the treatment of drug abuse and withdrawal and for eating disorders, other uses are also suggested by the studies discussed herein. Thus, cognitive disorders, brain trauma, memory loss, psychosis, sleep disorders, obsessive compulsive disorders, panic disorders, myasthenia gravis, Parkinson's disease, Alzheimer's disease, schizophrenia, Tourette's syndrome, Huntington's disease, attention deficit disorder, hyperkinetic syndrome, chronic nervous exhaustion, narcolepsy, pain, motion sickness and depression, and related conditions are considered to be susceptible to treatment with a compound of the present invention.

As shown by the results of the studies described herein, cis-2,6-di-trans-styrylpiperidine and trans-2,6-di-trans-styrylpiperidine are found to be effective in inhibiting uptake of extracellular 5-HT by serotonergic nerve terminals in the CNS, as well as in inhibiting the binding of [$^3$H]MTBZ to vesicle membranes indicating an interaction with VMAT2. These analogs are also nicotinic receptor antagonists, inhibiting nicotine-evoked [$^3$H]DA and [$^3$H]NE release from rat brain slices. Either or both mechanisms can thereby alter the distribution of the intracellular neurotransmitter pools, and as a result, alter extracellular neurotransmitter concentrations.

DETAILED DESCRIPTION OF THE INVENTION

The 2,6-disubstituted piperidine analogs of the present invention include those contemplated by the following formula (I), without regard to chirality:

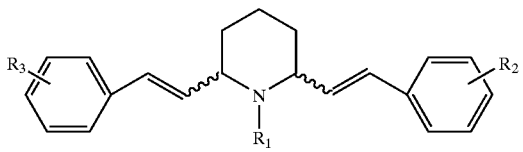

(I)

wherein:

$R^1$ represents a hydrogen, methyl, deuteromethyl ($CD_3$), tritiomethyl ($CT_3$), ethyl, or $C_3$–$C_7$ straight chain or branched alkyl (preferably methyl or ethyl), $C_3$–$C_6$ cycloalkyl, vinyl, allyl, $C_4$–$C_7$ alkenyl (including cis and trans geometrical forms), benzyl, and phenylethyl.

$R^2$ and $R^3$ are each independently ortho-, meta-, orpara-substituted moieties, where the substituent is described as hydrogen, methyl, ethyl, or $C_3$–$C_7$ straight chain or branched alkyl, $C_3$–$C_6$ cycloalkyl, vinyl, allyl, $C_4$–$C_7$ alkenyl (including cis and trans geometrical forms), benzyl, and phenylethyl. Further, the substitute moieties can be N-methylamino, N,N-dimethylamino, carboxylate, methylcarboxylate, ethylcarboxylate, propylcarboxylate, isopropylcarboxylate, carboxaldehyde, acetoxy, propionyloxy, isopropionyloxy, cyano, aminomethyl, N-methylaminomethyl, N,N-dimethylaminomethyl, carboxamide, N-methylcarboxamide, N,N-dimethylcarboxamide, acetyl, propionyl, formyl, benzoyl, sulfate, methylsulfate, hydroxyl, methoxy, ethoxy, propoxy, isopropoxy, thiol, methylthio, ethylthio, propiothiol, fluoro, chloro, bromo, iodo, trifluoromethyl, propargyl, nitro, carbamoyl, ureido, azido, isocyanate, thioisocyanate, hydroxylamino, and nitroso.

The above 2,6-substituted piperidino analogs are preferred in their 2,6-cis geometrical isomeric forms, or in their 2,6-trans geometric forms, including all possible geometric, racemic, diasteriomeric, and enantiomeric forms thereof.

The above 2,6-disubstituted piperidines as well as their analogs can be administered in their free base form or as a soluble salt. Whenever it is desired to employ a salt of a 2,6-substituted piperidine or its analog, it is preferred that a soluble salt be employed. Some preferred salts include hydrochloride, hydrobromide, nitrate, sulfate, phosphate, tartrate, galactarate, fumarate, citrate, maleate, glycolate, malate, ascorbate, lactate, aspartate, glutamate, methanesulfonate, p-toluenesulfonate, benzenesulfonate, salicylate, proprionate, and succinate salts. The above salt forms may be in some cases hydrates or solvates with alcohols and other solvents.

A pharmaceutical composition containing a compound of the invention is also contemplated, which may include a conventional additive, such as a stabilizer, buffer, salt, preservative, filler, flavor enhancer and the like, as known to those skilled in the art. Representative buffers include phosphates, carbonates, citrates and the like. Exemplary preservatives include EDTA, EGTA, BHA, BHT and the like. A composition of the invention may be administered by inhalation, i.e., intranasally as an aerosol or nasal formulation; topically, i.e., in the form of an ointment, cream or lotion; orally, i.e., in solid or liquid form (tablet, gel cap, time release capsule, powder, solution, or suspension in aqueous or non aqueous liquid; intravenously as an infusion or injection, i.e., as a solution, suspension or emulsion in a pharmaceutically acceptable carrier; transdermally, e.g., via a transdermal patch; rectally as a suppository and the like.

Generally, the pharmacologically effective dose of a present compound is in the amount ranging from about $1 \times 10^{-5}$ to about 1 mg/kg body weight/day. The amount to be administered depends to some extent on the lipophilicity of the specific compound selected, since it is expected that this property of the compound will cause it to partition into fat deposits of the subject. The precise amount to be administered can be determined by the skilled practitioner in view of desired dosages, side effects and medical history of the patient and the like.

The 2,6-disubstituted piperidino analogs of the present invention exhibit activity at either nAChRs and/or the serotonin transporter protein (SERT) and/or the vesicular monoamine transporter (VMAT2).

Compound 1

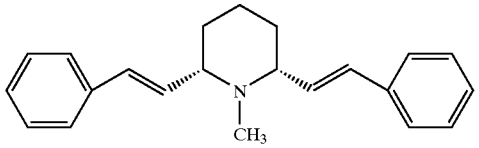

Cis-2,6-di-trans-styrylpiperidine

Compound 2

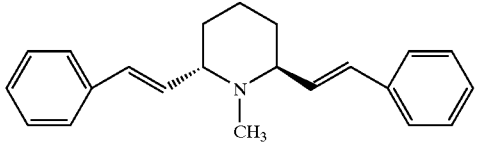

Trans-2,6-di-trans-styrylpiperidine

Table 1 below summarizes the interaction of cis-2,6-di-trans-styrylpiperidine (Compound 1) and trans-2,6-di-trans-styrylpiperidine (Compound 2) with nicotinic receptors, SERT and VMAT2.

TABLE 1

| Compound | [$^3$H]Nicotine Binding (Ki) α4β2* | [$^3$H]MLA Binding (Ki) α7* | Inhibition Nicotine-Evoked $^{86}$RB$^+$ Efflux[a] (IC$_{50}$) α4β2* | Inhibition of Nicotine-Evoked[$^3$H]DA Overflow [b](IC$_{50}$) α3β2* | Inhibition of Nicotine-Evoked[$^3$H]NE Overflow [b](IC$_{50}$) α3β4* | Inhibition of [$^3$H]MTBZ binding (IC$_{50}$) VMAT2 | [$^3$H]5-HT Uptake (IC$_{50}$) SERT |
|---|---|---|---|---|---|---|---|
| 1 | 11 μM | >100 μM | >10 μM | 0.03 μM | 0.021 | 1.29 μM | 23.2 μM |
| 2 | 13 μM | >100 μM | Not determined | 0.54 μM | Not determined | 5.15 μM | 1.19 μM |

[a]Inhibition of 1 μM S(-)-nicotine
[b]Inhibition of 10 μM S(-)-nicotine

The two 2,6-disubstituted piperidino derivatives in Table 1 have the chemical structure of Formula I, and were assayed for interaction with α4β*, α7*, α3β2*and α3β4*subtypes of nAChRs, interaction with VMAT2 located on vesicle membranes and inhibition of SERT function. It shall be noted that the nAChR subtypes for the activities described herein have not been elucidated conclusively, and thus, the asterisk is an indication of the putative nature of the receptor subtype mediating the action. Compound 1 exhibits good selectivity (43-fold) for the α3β2*subtype of nAChR relative to its interaction with the MTBZ site on VMAT2, as indicated by its ability to inhibit nicotine-evoked [$^3$H]DA release. Moreover, Compound 1 exhibits very good selectivity (>370-fold) for the α3β2*and α3β4*subtypes of nAChRs compared to its interaction with either α4β2*or α7*subtypes of nAChR. Furthermore, Compound 1 was 770-fold more selective as an inhibitor of the α3β2*and α3β4*subtypes of nAChR compared to its inhibition of SERT function. Finally, Compound 1 interacted with VMAT2 18-fold more selectively than it inhibited the function of SERT.

Compound 2 was also assayed for interaction with nAChRs subtypes, interaction with VMAT2 located on vesicle membranes and inhibition of SERT function. Compound 2 exhibits good selectivity (9.5-fold) for the α3β2*subtype of nAChR relative to its interaction with the MTBZ site on VMAT2, as indicated by its ability to inhibit nicotine-evoked [$^3$H]DA release. Moreover, Compound 2 exhibits very good selectivity (>24-fold) for the α3β2*subtype of nAChR compared to its interaction with either α4β2*or α7*subtypes of nAChR. Furthermore, Compound 2 was only 2.2-fold more selective as an inhibitor of the α3β2*subtypes of nAChR compared to its inhibition of SERT function. Finally, Compound 2 interacted with SERT 4.3-fold more selectively than it interacted with VMAT2.

Compound 1 was 18-fold more potent at inhibiting nicotine-evoked [$^3$H]DA and [$^3$H]NE release from rat striatal and hippocampal slices, indicated a higher affinity for the α3β2*and α3β4*subtypes of nAChRs, compared to Compound 2. On the other hand, Compound 2 was 19-fold more potent inhibiting the function of SERT than was Compound 1. Finally, Compound 1 was only 4-fold more potent interacting with VMAT2 compared to Compound 2. Thus, alteration of stereochemistry at C2 and C6 from cis to trans resulted in a diminished affinity for the α3β2*subtypes of nAChR and for VMAT2, and enhanced the affinity for SERT, whereas there was no change in affinity for either α4β2*or α7*subtypes of nAR. Therefore, cis-analogs have higher affinity for VMAT2 and α3β2*subtype of nAChRs.

The invention will now be discussed by certain examples which illustrate but do not limit the invention.

EXAMPLE 1

Scheme 1: Synthesis of cis- and trans-2,6-di-trans-styrylpiperidine
Preparation of Cis- and trans-2,6-di-trans-styrylpiperidine

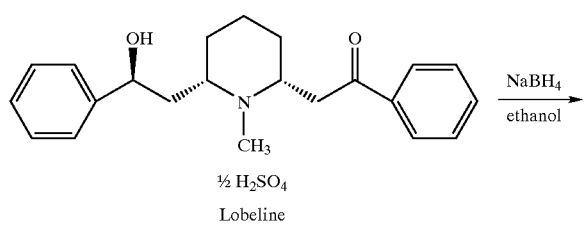

Lobeline

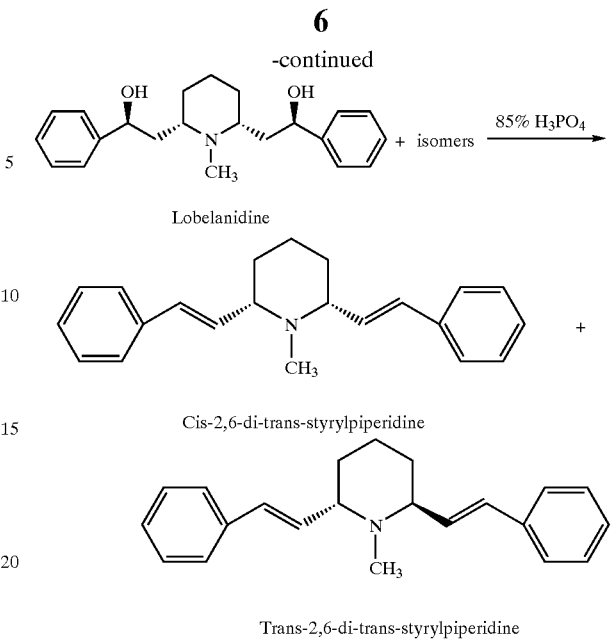

Lobelanidine

Cis-2,6-di-trans-styrylpiperidine

Trans-2,6-di-trans-styrylpiperidine

To a suspension of L-lobeline hemisulfate salt (85%, 10.5 g) in absolute ethanol (300 mL) was added NaBH$_4$ (1.5 eq.) portionwise at 0° C. The mixture was stirred at 0° C. for 1 h, and then quenched with acetone. The mixture was evaporated under reduced pressure. Water (100 mL) was added to the residue and extracted with chloroform (80 mL×3). The combined organic extract was dried (MgSO$_4$), filtered and evaporated to afford lobelanidine as a white solid which was used directly. An analytical sample was recrystallized from acetone/hexane as a needle crystal. Mp 142–143° C; $^1$H NMR (300 MHz, CDCl$_3$) δ 1.15 (m, 2H), 1.44–1.82 (m, 6H), 2.04 (ddd, J=14.4, 10.2, 8.7 Hz, 2H), 2.35 (s, 3H), 2.96 (m, 2H), 4.89 (dd, J=8.7, 5.5 Hz, 2H), 7.23–7.50 (m, 10H); $^{13}$C NMR (75 MHz, CDCl$_3$) δ 23.48, 25.20, 25.96, 41.79, 62.37, 74.30, 125.98, 127.50, 128.55, 144.88 ppm.

Crude lobelanidine was dissolved in 130 mL 85% H$_3$PO$_4$ and allowed to stir at 60° C. for 24 h. The reaction mixture was cooled to room temperature, diluted with 250 mL water and made basic with solid NaOH (pH~10). The aqueous solution was extracted with EtOAc (150 mL×3) The combined organic extract was dried (MgSO$_4$), filtered and concentrated under reduced pressure. The crude product was recrystallized from acetone affording 2.2 g of pure cis-2,6-di-trans-styrylpiperidine as a white solid. Mp: 105–106° C. (HCl salt); $^1$H NMR (300 MHz, CDCl$_3$) δ 1.42–1.88 (m, 6H), 2.25 (s, 3H), 2.63 (m, 2H), 6.21 (dd, J=15.9, 9.0, 2H), 6.51 (d, J=15.9, 2H), 7.19–7.41 (m, 10H); $^{13}$C NMR (75 MHz, CDCl$_3$) δ 24.14, 33.94, 42.61, 68.56, 126.32, 127.46, 128.69, 130.51, 134.03, 137.17 ppm. The remaining mother liquor was evaporated and the residue was chromatographed (SiO$_2$, EtOAc/hexanes, 1/10) to afford cis-2,6-di-trans-styrylpiperidine 1.4g and trans-2S,6S-di-trans-styrylpiperidine 230 mg. Mp: 200–202° C. (HCl salt); $^1$H NMR (300 MHz, CDCl$_3$) δ 1.60–1.75 (m, 4H), 1.82–1.97 (m, 2H), 2.27 (s, 3H), 3.38 (m, 2H), 6.38 (dd, J=15.9, 8.7, 2H), 6.52 (d, J=15.9, 2H), 7.17–7.42 (m, 10H); $^{13}$C NMR (75 MHz, CDCl$_3$) δ 19.57, 32.92, 41.96, 62.29, 126.39, 127.50, 128.69, 130.49, 131.78, 137.20 ppm.

EXAMPLE 2

High Affinity [$^3$H]Nicotine Binding Assay

The ability to displace S(−)[$^3$H]nicotine binding from rat striatal membranes which assessed the α4β2*subtype was determined. The [$^3$H]nicotine binding assay was performed according to previously published methods (Romano et al., 1980; Marks et al., 1986; Crooks et al., 1995). Striata from two rats were dissected, pooled and homogenized with a Tekmar polytron in 10 vol of ice-cold modified Krebs-HEPES buffer (20 mM HEPES, 118 niM NaCl, 4.8 mM KCl, 2.5 mM CaCl$_2$, 1.2 mM MgSO$_4$, adjusted to pH to 7.5). The homogenate was incubated at 37° C. for 5 min to promote hydrolysis of endogenous acetylcholine, and centrifuged at 27,000 g for 20 min and the pellet was resuspended in 10 vol of ice-cold distilled water and incubated at 37° C. for 5 min, followed by centrifugation at 27,000 g for 20 min. The pellet containing the striatal membranes was resuspended in 10 vol of fresh ice-cold 10% Krebs-HEPES buffer and incubated at 37° C. for 10 min after which it was centrifuged at 27,000 g for 20 min. The latter sequence of resuspension, incubation and centrifugation was repeated. The pellet was frozen under fresh Krebs-HEPES buffer and stored at −40° C. until assay. Upon assay, the pellet was resuspended in Krebs-HEPES buffer, incubated at 37° C. for 5 min and centrifuged at 27,000 g for 20 min. The final pellet was resuspended in 3.6 mL ice-cold water, which provides for approximately 200 μg protein/100 μL aliquot, as defined by the Bradford dye binding method (Bradford, 1976) using bovine serum albumin (BSA) as the standard. Competition assays were performed in duplicate in a final vol of 200 μL Krebs-HEPES buffer containing 250 mM Tris buffer (pH 7.5 at 4° C.). Reactions were initiated by addition of 100 μL of membrane suspension to 3 nM [$^3$H]nicotine (L-(−)-[N-methyl-$^3$H]nicotine; 50 μL, specific activity 69.5 Ci/mMol ) and 1 of at least 9 concentrations of analog (50 μL). After a 90 min incubation at 4° C., reactions were terminated by dilution of the samples with 3 mL of ice-cold buffer followed immediately by filtration through a Whatman GF/B glass fiber filters (presoaked in 0.5% polyethyleneimine using a Brandel cell harvester). Filters were rinsed 3 times with 3 mL of ice-cold buffer, transferred to scintillation vials and 5 mL scintillation cocktail added. Nonspecific binding was defined as binding in the presence of 10 μM S(−)-nicotine. For competition curves, the IC$_{50}$ values were corrected for ligand concentration to obtain Ki values for each analog (Cheng et al., 1973).

EXAMPLE 3

[$^3$H]Methyllycaconitine ([$^3$]HIMLA)Binding Assay

Whole rat brain (minus cortex, striatum and cerebellum) was homogenized in 20 vol of ice-cold hypotonic buffer (2 mM HEPES, 14.4 mM NaCl, 0.15 mM KCl, 0.2 mM CaCl$_2$ and 0.1 mM MgSO$_4$, pH 7.5). Homogenates were incubated at 37° C. for 10 min and centrifuged at 25,000 g for 15 min at 4° C. Pellets were washed 3 times by resuspension in 20 vol of the same buffer and centrifugation using the above parameters. Final pellets were resuspended in incubation buffer to provide ~150 μg protein/100 μL. Binding assays were performed in duplicate, in a final vol of 250 μL incubation buffer, containing 20 mM HEPES, 144 mM NaCl, 1.5 mM KCl, 2 mM CaCl$_2$, 1 mM MgSO$_4$ and 0.05% BSA, pH 7.5. Assays were initiated by the addition of 100 μL membrane suspension to 150 μL of sample containing 2.5 nM [$^3$H]MLA ([1α, 4(S), 6β, 14α, 16β]-20-ethyl-1,6,14,16-tetramethoxy-4[[[2-(-[3-$^3$H]-methyl-2,5-dioxo-1-pyrrolidinyl)benzoyl]oxy]methyl]aconitane-7,8-diol; specific activity 26.2 Ci/mMol) and at least 6 concentrations (30 nM–100 μM) synthetic analog (final concentrations), and incubated for 2 h at room temperature. Nonspecific binding was determined in the presence of 10 μM MLA. Assays were terminated by dilution of samples with 3 mL ice-cold incubation buffer followed by immediate filtration through Schleicher & Schuell #32 glass fiber filters (Keene, NH; presoaked with 0.5% PEI) using the cell harvester. Filters were rinsed 3 times with 3 mL of ice-cold buffer, transferred to scintillation vials, 4 mL of scintillation cocktail added, and bound radiolabel determined by liquid scintillation spectroscopy. Protein was measured using the Bradford dye-binding method (Bradford, 1976) with BSA as the standard.

EXAMPLE 4

[$^3$H]Methoxytetrabenazine [$^3$H]MTBZ Binding Assay

Synaptic vesicles were prepared from rat brain using a modification of a previously described procedure (Teng et al., 1998). Briefly, fresh whole brain (excluding cerebellum) was homogenized using a Teflon pestle (clearance 0.003 mm) with 7 vertical strokes at 800 rpm in 20 vol of ice-cold 0.32 M sucrose and centrifuged at 1000 g for 12 min at 4° C. The resulting supernatant (S$_1$) was then centrifuged at 22,000 g for 10 min at 4° C. The synaptosomal pellets (P$_2$) were homogenized in 18 mL of ice-cold Milli-Q water and exposed for 5 min for lysing synaptosomes. Osmolarity was restored by addition of 2 mL of 25 mM HEPES with 100 mM dipotassium tartrate (pH 7.5). Samples were centrifuged at 20,000 g for 20 min at 4° C. to remove lysed synaptosomal membranes. MgSO$_4$ (1 mM) was added to the supernatant (S$_3$), and was centrifuged at 100,000 g for 45 min at 4° C. The final vesicular pellets (P$_4$) were resuspended in ice-cold assay buffer (see below) providing ~15 μg protein/100 μL, determined by the method of Bradford (1976) using bovine serum albumin as a the standard. Aliquot parts (100 μL) of suspension of vesicle membrane protein were incubated in assay buffer (25 mM HEPES, 100 mM dipotassium tartrate, 5 mM MgSO$_4$, 0.1 mM EDTA and 0.05 mM EGTA, pH 7.5, at 25° C.) in the presence of 3 nM [$^3$H]MTBZ ([O-methyl -$^3$H]methoxytetrabenazine) and at least 7 concentrations (1 nM–1 mM) of analog for 1 hr at room temperature. Nonspecific binding was determined in the presence of 20 μL TBZ. Assays were performed in duplicate using a 96-well plate format. Reactions were terminated by filtration of samples on a Unifilter-96 GF/B filter plates (presoaked in 0.5% polyethylenimine), using a FilterMate harvester (Packard BioScience Co., Meriden, Conn.). After washing 5 times with 350 μL of the ice-cold wash buffer (25 mM HYEPES, 100 mM dipotassium tartrate, 5 mM MgSO$_4$ and 10 mM NaCl, pH 7.5), filter plates were dried, sealed and each well filled with 40 μL Packard's MicroScint 20 cocktail. Bound [$^3$H]MTBZ was measured using a Packard TopCount NXT scintillation counter with a Packard Windows NT based operating system.

EXAMPLE 5

[$^3$H]5-HT Uptake Assay

[$^3$H]5-HT uptake was assessed using modifications of a previously described method (Teng et al., 1998). Nonspecific uptake was determined in duplicate samples in the presence of excess (10 μM) fluoxetine. Rat hippocampus was homogenized in 20 mL cold 0.32 M sucrose containing 5 mM NaHCO$_3$ (pH 7.4) with 12 vertical strokes of a Teflon pestle homogenizer (clearance~0.015 mm). The homogenate was centrifuged (2,000×g for 10 min at 4° C.). The supernatant was centrifuged (20,000×g for 15 min at 4° C.), and then the pellet was resuspended in 1.5 mL of Kreb's buffer (125 mM NaCl, 5 mM KCl, 1.5 mM MgSO$_4$, 1.25 mM CaCl$_2$, 1.5 mM KH$_2$PO$_4$, 10 mM α-D-glucose, 25 mM HEPES, 0.1 mM disodium ethylenediamine tetraacetate, 0.1 mM pargyline and 0.1 mM ascorbic acid, saturated with 95% O$_2$/5% CO$_2$, pH 7.4). Final protein concentration was 400 μg/mL, determined using BSA standard (Bradford, 1976). The assay was performed in duplicate in a total vol of 500 μL. Aliquot parts of synaptosomal suspension (50 μL) were added to tubes containing 350 μL Kreb's buffer and 50 μL of buffer containing 1 of 9 concentrations of analog. Tubes were preincubated at 34° C. for 10 min before addition of 50 μL of [$^3$H]5-HT (5-[1,2-$^3$H(N)]-hydroxytryptamine; specific activity 25.5 Ci/mMol, final concentration 10 nM). Accumulation proceeded for 10 min at 34° C. Reactions were terminated by addition of 3 mL ice-cold Kreb's buffer. Samples were rapidly filtered through a Whatman GF/B filter using a cell harvester (MP-43RS, Brandel Inc., Gaithersburg, Md.), and the filter was subsequently washed 3 times with 4 mL ice-cold Kreb's buffer containing catechol (1 mM). Filters were previously soaked for 2 hours in the ice-cold Kreb's buffer containing catechol (1 mM). Radioactivity on filters was determined by liquid scintillation spectroscopy.

EXAMPLE 6

[$^3$H]Dopamine and [$^3$H]Norepineplhrine Release Assay

Alkaloid effects on [$^3$H]overflow from rat striatal slices preloaded with [3H]DA and hippocampal slices preloaded with [$^3$H]NE were determined using modifications of a previously published method (Dwoskin and Zahniser, 1986). Briefly, coronal striatal or hippocampal slices (500 μm, 6–8 mg) were incubated in Krebs' buffer (118 mM NaCl, 4.7 mM KCl, 1.2 mM MgCl$_2$, 1.0 mM NaH$_2$PO$_4$, 1.3 mM CaCl$_2$, 11.1 mM α-D-glucose, 25 mM NaHCO3, 0.11 mM L-ascorbic acid and 4.0 mM disodium ethylenediaminetetraacetate; pH 7.4, and saturated with 95% O$_2$/5% CO$_2$) in a metabolic shaker at 34° C. for 30 min. Striatal or hippocampal slices were incubated in fresh buffer (6–8 slices/3 mL) containing 0.1 μM [$^3$H]DA (3,4-[7-$^3$H]-dihydroxyphenylethylamine; specific activity 28 Ci/mMol) or 0.1 μM [$^3$H]NE (levo-[7-$^3$H]-norepinephrine; specific activity 14.4 Ci/mMol), respectively, for an additional 30 min. After rinsing, each slice was transferred to a glass superfusion chamber maintained at 34° C. and was superfused at 1 mL/min with oxygenated Krebs' buffer containing pargyline (10 μM) and nomifensine (10 μL) or pargyline and desipramine (10 μL) in experiments assessing [$^3$H]DA and [$^3$H]NE overflow, respectively. After 60 min of superfusion, three 5-min samples (5 mL) were collected to determine basal [$^3$H]outflow. After collection of the third basal sample, slices from an individual rat were superfused in the absence or presence of a single concentration of analog, which remained in the buffer until the end of the experiment. Each slice was exposed to only one concentration of analog. After 30 min, S(−)-nicotine (10 μM) was added to the buffer containing analog, and superfusion continued for an additional 60 min. These experiments utilized a repeated measures design, such that the analog concentration-effect was determined in both the absence and presence of S(−)-nicotine using striatal or hippocampal slices from a single rat. Additionally, one striatal or hippocampal slice was superfused in the absence of analog and constituted the control condition. At the end of the experiment, each slice was solubilized with TS-2. The pH and volume of the solubilized tissue samples were adjusted to those of the superfusate samples. Radioactivity in the superfusate and tissue samples was determined by liquid scintillation spectroscopy (Packard model B1600 TR Scintillation Counter, Downer's Grove, Ill.).

EXAMPLE 7

$^{86}$Rb$^+$ Rubidium Efflux Assay

Analog effects on $^{86}$Rb$^+$ efflux were determined using a previously published method (Miller et al., 2000). Thalamus was homogenized and centrifuged at I1000×g for 10 min at 4° C. The supernatant fraction was centrifuged at 12,000×g for 20 min at 4° C. to obtain the synaptosomal fraction. Synaptosomes were incubated for 30 min in 35 μL of uptake buffer (1.40 mM NaCl, 1.5 mM KCl, 2.0 mM CaCl$_2$, 1.0 mM MgSO$_4$, 20 mM α-D-glucose; pH 7.5) containing 4 μCi of $^{86}$Rb$^+$. $^{86}$Rb$^+$ uptake was terminated by filtration of the synaptosomes onto glass fiber filters (6 mm; Type A/E, Gelman Sciences, Ann Arbor, Mich.) under gentle vacuum (0.2 atm), followed by three washes with superfusion buffer (0.5 mL each). Subsequently, each filter with $^{86}$Rb$^+$-loaded synaptosomes (40 μg protein/μl) was placed on a 13 mm glass fiber filter (Type A/F) mounted on a polypropylene platform. $^{86}$Rb$^+$ efflux assay buffer (125 mM NaCl, 5 mM CsCl, 1.5 mM KCl; 2 mM CaCl$_2$, 1 mM MgSO$_4$, 25 mM HEPES, 20 mM α-D-glucose, 0.1 μM tetrodotoxin, 1.0 g/L bovine serum albumin; pH 7.5) was superfused onto the synaptosomes at a rate of 2.5 mL/min. Tetrodotoxin and CsCl were included in the buffer to block voltage-gated Na$^+$ and K$^+$ channels, respectively, and to reduce the rate of basal $^{86}$Rb$^+$ efflux. The ability of analogs to inhibit $^{86}$Rb$^+$ efflux evoked by 1 μM nicotine was determined. After 8 min of superlusion, samples were collected (sample/18 s) for 5 min to determine basal $^{86}$Rb$^+$ efflux. Subsequently, synaptosomes were superfused for 3 min with analog followed by superfusion with buffer containing analog and nicotine for an additional 3 min. Each aliquot part of thalamic synaptosomes was exposed to only one concentration of analog. In each experiment, one synaptosomal aliquot part was superfused in the absence of analog to determine basal $^{86}$Rb$^+$ efflux over the course of the superfusion period, and another aliquot part was superfused with nicotine (1 μM) to determine the effect of nicotine on $^{86}$Rb$^+$ efflux in the absence of analog. Samples were analyzed by liquid scintillation spectroscopy (Packard model B1600 TR Scintillation Counter).

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalence thereof may be resorted to, falling within the scope of the invention claimed.

References

The pertinent disclosures of the references listed below and as discussed above herein are incorporated herein by reference.

Barlow R. B. et al., "Relations between structure and nicotine-like activity: X-ray crystal structure analysis of (−)cystine and (−)lobeline hydrochloride and a comparison with (−) nicotine and other nicotine-like compounds," *Br. J. Pharmacol.*, 1989; 98: 799–808.

Bradford M M, "A rapid and sensitive method for the quantitation of microgram quantities of protein utilizing the principle of protein-dye binding. *Ann. Biochem.*, 1976; 72: 248–253.

Broussolle E. P. et al., "In vivo binding of [3H]-nicotine in the mouse brain," *Life Sciences*, 1989; 44: 1123–1132.

Cheng Y. C. et al., "Relationship between the inhibition constant ($K_i$) and the concentration of inhibitor which causes 50 percent inhibition ($I_{50}$) of an enzymatic reaction," *Biochem. Pharmacol.*, 1973; 22: 3099–3108.

Clarke P. B. S. et al., "Release of [3H]noradrenaline from rat hippocampal synaptosomes by nicotine: mediation by different nicotinic receptor subtypes from striatal [3H] dopamine release," *Br. J. Pharmacol.*, 1993; 45: 571–576.

Crooks P. A. et al., "Inhibition of nicotine-evoked dopamine release by pyridino-N-rsubstituted nicotine analogues: a new class of nicotinic antagonist," *Drug Dev. Res.*, 1995; 36; 71–82.

Decker M. W. et al., "Effects of lobeline, a nicotinic receptor agonist, on learning and memory," *Pharmacol. Biochem. Behav.* 1993; 45: 571–576.

Dwoskin L. P. and Zahniser N. R., "Robust modulation of [3H]dopamine release from rat striatal slices by D-2 dopamine receptors. *J. Pharmacol. Exp. Ther.* 1986; 239: 442–453.

Dwoskin L. P. et al., "S-(−)-Cotinine, the major brain metabolite of nicotine, stimulates nicotinic receptors to evoke [3H]dopamine release from rat striatal slices in a calcium-dependent manner," *J. Pharmacol. Exp. Therap.*, 1999; 288: 905–911.

Hamann S. R. et al., "Hyperalgesic and analgesic actions of morphine, U50-488, naltrexone, and (−)lobeline in the rat brainstem," *Pharmacol. Biochem. Behav.*, 1994; 47: 197–201.

Lippiello P. M. et al., "The binding of L-[3H]nicotine to a single class of high affinity sites in rat brain membrane," *Mol. Pharmacol.*, 1986; 29: 448–454.

Marks M. J. et al., "Nicotine binding sites in rat and mouse brain: comparison of acetylcholine, nicotine and α-bungarotoxin," *Mol. Pharmacol.*, 1986; 30: 427–436.

Miller D. K et al., "Lobeline inhibits nicotine-evoked [3H]dopamine overflow from rat striatal slices and nicotine-evoked $^{86}Rb^+$ efflux from thalamic synaptosomes. *Neuropharmacology*, 2000; 39:2654–2662.

Olin B. R. et al., *Drug Facts and Comparisons*, JB Lippincott Co., St. Louis, Mo., pp 3087–3095 (1995).

Romano C. et al., "Stereospecific nicotinic receptors on rat brain membranes," *Science*, 1980; 210: 647–650.

Teng L. H. et al., "Lobeline and nicotine evoke [3H]-overflow from rat striatal slices reloaded with [3H] dopamine: differential inhibition of synaptosomal and vesicular [3H]dopamine uptake," *J. Pharmacol. Exp. Therap.*, 1997; 80: 1432–1444.

Teng L. H. et al, "Lobeline displaces [3H] dihydrotetrabenazine binding and releases [3H]dopamine from rat sriatal synaptic vesicles," *J. Neurochem.*, 1998; 71: 258–265.

What is claimed is:

1. A method of treating an individual for dependence on or withdrawal from a drug of abuse, for an eating disorder or for a CNS disease or pathology, comprising the step of administering to the individual an effective amount of a 2,6-substituted piperidino compound and pharmaceutically effective salts thereof, including resolved diasteriomers, enantiomers thereof, of the formula (I):

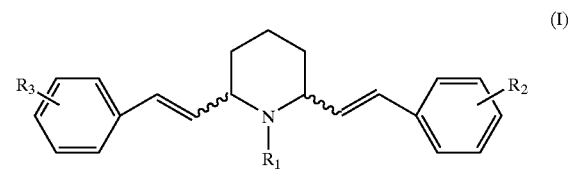

wherein:

$R^1$ represents a hydrogen, methyl, deuteromethyl ($CD_3$), tritiomethyl ($CT_3$), ethyl, or $C_3$–$C_7$ straight chain or branched alkyl, $C_3$–$C_6$ cycloalkyl, vinyl, allyl, $C_4$–$C_7$ alkenyl, benzyl, and phenylethyl;

$R^2$ and $R^3$ are each independently ortho-, meta-, or para-substituted moieties, where the substituted moiety is selected from the group consisting of hydrogen, methyl, ethyl, $C_3$–$C_7$ straight chain or branched alkyl, $C_3$–$C_6$ cycloalkyl, vinyl, allyl, $C_4$–$C_7$ alkenyl, benzyl, phenylethyl, N-methylamino, N,N-dimethylamino, carboxylate, methylcarboxylate, ethylcarboxylate, propylcarboxylate, isopropylcarboxylate, carboxaldehyde, acetoxy, propionyloxy, isopropionyloxy, cyano, aminomethyl, N-methylaminomethyl, N,N-dimethylaminomethyl, carboxamide, N-methylcarboxamide, N,N-dimethylcarboxamide, acetyl, propionyl, formyl, benzoyl, sulfate, methylsulfate, hydroxyl, methoxy, ethoxy, propoxy, isopropoxy, thiol, methylthio, ethylthio, propiothiol, fluoro, chloro, bromo, iodo, trifluoromethyl, propargyl, nitro, carbamoyl, ureido, azido, isocyanate, thioisocyanate, hydroxylamino, and nitroso.

2. The method of claim 1, wherein $R^1$ is methyl or ethyl.

3. The method of claim 1, wherein $R^1$ is methyl.

4. The method of claim 1, wherein the 2,6-substituted piperidino compound or pharmaceutically effective salt thereof is cis-2,6-di-trans-styrlpiperidine having the following formula (II):

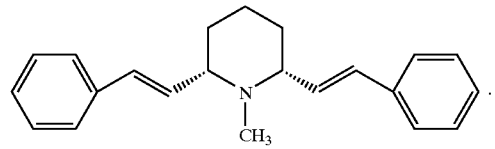

5. The method of claim 1, wherein the 2,6-substituted piperidino compound or pharmaceutically effective salt thereof is trans-2,6-di-trans-styrlpiperidine having the following formula (II):

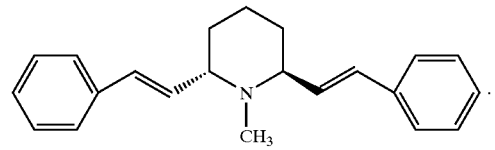

6. The method of claim 1 wherein said drug of abuse is selected from the group consisting of cocaine, amphetamine, caffeine, nicotine, phencyclidine, opiates, barbiturates, benzodiazepines, canabinoids, hallucinogens and alcohol.

7. The method of claim 1 wherein in said CNS disease or pathology is selected from the group consisting of cognitive disorders, brain trauma, memory loss, psychosis, depression, sleep disorders, obsessive compulsive disorders, panic disorders, myasthenia gravis, Parkinson's disease, Alzheimer's disease, schizophrenia, Tourette's syndrome, Huntington's disease, attention deficit disorder, hyperkinetic syndrome, chronic nervous exhaustion, narcolepsy, motion sickness and the control of pain.

8. The method of claim 1 wherein said 2,6-substituted piperidino compound or pharmaceutically effective salt thereof is administered subcutaneously, intramuscularly, intravenously, transdermally, orally, intranasally, intrapulmonary or rectally.

9. The method of claim 1 wherein said 2,6-substituted piperidino compound or pharmaceutically effective salt thereof inhibits release, uptake and storage of DA, NE and 5-HT by cells of the central nervous system of the individual.

* * * * *

UNITED STATES PATENT AND TRADEMARK OFFICE
Certificate

Patent No. 6,703,406 B2                                                          Patented: March 9, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Peter A. Crooks, Lexington, KY (US); Linda Dwoskin, Lexington, KY (US); Dennis Keith Miller, Lexington, KY (US); Vladimir P. Grinevich, Lexington, KY (US); Seth Davin Norrholm, Lexington, KY (US); Guangrong Zheng, Lexington, KY (US); and Marlon D. Jones, Compton, CA (US).

Signed and Sealed this Twenty-sixth Day of December 2006.

WILLIAM R. DIXON, JR.
*Special Programs Examiner*
Art Unit 1600

UNITED STATES PATENT AND TRADEMARK OFFICE
CERTIFICATE OF CORRECTION

| | | |
|---|---|---|
| PATENT NO. | : 6,703,406 B2 | Page 1 of 1 |
| APPLICATION NO. | : 10/163633 | |
| DATED | : March 9, 2004 | |
| INVENTOR(S) | : Crooks et al. | |

It is certified that error appears in the above-identified patent and that said Letters Patent is hereby corrected as shown below:

Title page, item (75) Inventors: address of inventor Vladimir P. Grinevich, should read --Winston-Salem, NC (US)--

Signed and Sealed this

Eighth Day of May, 2007

JON W. DUDAS
*Director of the United States Patent and Trademark Office*